United States Patent [19]

Engel et al.

[11] Patent Number: 4,503,269

[45] Date of Patent: Mar. 5, 1985

[54] ISOMERIZATION OF CRESOLS

[75] Inventors: Dusan J. Engel, Des Plaines; Thomas P. Malloy, Lake Zurich; James P. Shoffner, Elk Grove Village, all of Ill.

[73] Assignee: UOP Inc., Des Plaines, Ill.

[21] Appl. No.: 534,225

[22] Filed: Sep. 21, 1983

[51] Int. Cl.$^3$ .................... C07C 37/48; C07C 37/00
[52] U.S. Cl. ..................................... 568/783; 568/716
[58] Field of Search ..................... 568/715, 783, 716

[56] References Cited

U.S. PATENT DOCUMENTS

| | | | |
|---|---|---|---|
| 2,551,628 | 5/1951 | Nickels | 568/783 |
| 3,655,780 | 4/1972 | Kohn et al. | 568/783 |
| 3,702,886 | 11/1972 | Argauer et al. | 423/328 |
| 4,283,571 | 8/1981 | Keim et al. | 568/783 |

FOREIGN PATENT DOCUMENTS

| | | | |
|---|---|---|---|
| 0135944 | 11/1978 | Japan | 568/783 |
| 695464 | 8/1953 | United Kingdom | 568/783 |
| 748269 | 4/1966 | United Kingdom | 568/783 |
| 2012271 | 7/1979 | United Kingdom | 568/783 |

Primary Examiner—Werren B. Lone
Attorney, Agent, or Firm—James R. Hoatson, Jr.; Raymond H. Nelson; William H. Page, II

[57] ABSTRACT

An improvement in a process for the isomerization of cresols may be obtained by effecting the isomerization reaction of a cresol in the presence of a crystalline aluminosilicate zeolite catalyst and added hydrogen. The added hydrogen will provide stability and longer life to the catalyst as well as a more stable selectivity to the desired isomers. The isomerization reaction is effected at temperatures ranging from about 250° to about 450° C. and pressures ranging from 2 to about 75 atmospheres in the presence of added hydrogen, said hydrogen being present in a mole ratio in the range of from about 1:1 to about 10:1 moles of hydrogen per mole of cresol.

7 Claims, No Drawings

ISOMERIZATION OF CRESOLS

BACKGROUND OF THE INVENTION

Cresols may be prepared by the catalytic methylation of phenol. During the preparation, the predominant isomer which is obtained comprises o-cresol. While this particular isomer finds a wide variety of uses such as a disinfectant, as an inorganic intermediate or in the preparation of coumarine, the other isomers such as m-cresol and p-cresol are also important articles of commerce in the chemical industry. For example, m-cresol in addition to being utilized as a disinfectant, will also find a use in fumigating compositions, in the production of synthetic resins, as a photographic developer, in nitrocresol explosives, as a use in ink, paint and varnish removers or in reclaiming rubber. Additionally, p-cresol is also used as a disinfectant, in fumigating composition, in die stuffs and as an organic intermediate, etc. It is therefore encumbent to isomerize the predominantly o-cresol to the m and p isomers.

One such method for the isomerization of o-cresol is found in U.S. Pat. No. 4,283,571. This patent teaches the catalytic isomerization of o-cresol by utilizing an acid-acting crystalline aluminosilicate zeolite of the ZSM-type. The patent describes that the crystal structure of the zeolite should possess a pore dimension greater than about 5 Angstroms and a constraint index of from about 1.0 to about 12.0. The crystalline aluminosilicate zeolites will possess a definite crystalline structure in which are positioned a relatively large number of small cavities which are interconnected by a number of still smaller channels. The zeolites are known to possess catalytic properties, especially concerning those processes found in the petroleum refining field. These processes include cracking, hydrocracking, isomerization of n-paraffins and naphthenes, polymerization of compounds containing an olefinic or acetylenic linkage, reforming, alkylation, etc. The zeolite materials which are preferred for many of these processes possess a constraint index within the range hereinbefore set forth as well as containing a silica to alumina mole ratio between about 10 and about 85. An example of a crystalline aluminosilicate zeolite which may be used comprises that type which is set forth in U.S. Pat. No. 3,702,886.

While the process for the isomerization of cresols, and particularly o-cresol, utilizing a crystalline aluminosilicate zeolite catalyst in the reaction is known, we have now discovered that by effecting the reaction in the presence of hydrogen it is possible to obtain many beneficial and unexpected results, these results being hereinafter set forth in greater detail.

SUMMARY OF THE INVENTION

This invention relates to a process for the isomerization of cresols. More specifically, the invention is concerned with an improvement in the isomerization of cresols utilizing a crystalline aluminosilicate zeolite material as the catalyst for the reaction.

As hereinbefore set forth, the isomeric cresols are useful articles in the chemical industry. The isomerization of the predominant o-cresol fraction to the m and p isomers thereof has been effected by utilizing a zeolitic material as the catalyst for the reaction. However, we have now discovered that by effecting the isomerization reaction in the presence of added hydrogen, many beneficial effects can be obtained. As will hereinafter be shown in greater detail in the examples, by utilizing hydrogen in the reaction, it is possible to increase the life of the catalyst with a concomitant more uniform conversion of the cresol isomer undergoing isomerization. Another advantage which is found when employing hydrogen is an improvement in the selectivity to the p-cresol isomer along with an increase in the amount of total cresols, thereby minimizing the loss of aromatic compounds. Furthermore, another advantage which is found when employing hydrogen is a strong improvement in the color of the product.

It is therefore an object of this invention to provide a process for the isomerization of cresols.

A further object of this invention is to provide an improvement in a process for the isomerization of cresols utilizing a zeolitic catalyst in the reaction whereby improved results may be obtained thereby.

In one aspect an embodiment of this invention is found in a process for the isomerization of a cresol which comprises treating said cresol in the presence of a catalyst comprising a crystalline aluminosilicate zeolite at treatment conditions and recovering the resultant isomerized product, the improvement which comprises effecting said isomerization treatment in the presence of hydrogen.

A specific embodiment of this invention is found in a process for the isomerization of o-cresol which comprises treating said cresol at a temperature in the range of from about 250° to about 450° C., a pressure in the range of from about 2 to about 75 atmospheres, a Liquid Hourly Space Velocity in the range of from about 0.1 to about 6 hrs.$^{-1}$, in the presence of a catalyst comprising an acid-acting crystalline aluminosilicate and hydrogen, said hydrogen being present in a mole ratio in the range of from about 1:1 to about 10:1 moles of hydrogen per mole of cresol, and recovering the resultant isomerized product comprising m-cresol and p-cresol.

Other objects and embodiments will be found in the following further detailed description of the invention.

DETAILED DESCRIPTION OF THE INVENTION

As hereinbefore set forth, the present invention is concerned with an improvement in a process for the isomerization of a cresol whereby certain advantages previously mentioned may be attained. The extension of the stability and lifetime of the catalyst which is employed in the reaction will have a beneficial result in the overall cost of the process, thereby contributing to the commerical attractiveness of this process. The isomerization process is effected by treating a cresol such as o-cresol or m-cresol at treatment conditions in the presence of a crystalline aluminosilicate zeolite, the improvement which comprises effecting the process in the presence of added hydrogen.

As was previously mentioned, the crystalline aluminosilicate zeolite which is employed as the catalyst for the present process possesses a constraint index of from about 1.0 to about 12.0 and also possesses a silica to alumina ratio of from about 10 to about 85. The treatment conditions which are employed to effect the isomerization will include temperatures ranging from about 250° to about 450° C. and preferably in a range of from about 325° to about 400° C.; a pressure in the range of from about 2 to about 75 atmospheres and preferably in a range of from about 15 to about 60 atmospheres; and a Liquid Hourly Space Velocity in a range of from about 0.1 to about 6 and preferably from about 1 to about 3 hrs.$^{-1}$. The pressures which are employed at treatment conditions will be afforded by the addition of hydrogen which is charged to the reactor in an amount so that the hydrogen present will be in a molar ratio of from about 1:1 to about 10:1 and preferably from about 2:1 to about 6:1 moles of hydrogen per mole of cresol. Alternatively, if so desired, the operating pressures which are employed may be afforded by a partial pressure of hydrogen, the remainder being afforded by the addition of an inert gas such as nitrogen, helium, argon into the reaction vessel so that the preferred operating pressure is attained.

The isomerization of the o-cresol or m-cresol may be effected in any manner, either by a batch type operation or a continuous type operation. For example, when a batch type operation is employed, a quantity of the cresol along with the catalyst is placed in an appropriate apparatus such as an autoclave of the rotating, mixing or stirring type. The autoclave is sealed and hydrogen is pressed in until the desired initial operating pressure has been reached. Following this, the autoclave and contents thereof are heated to the desired operating temperature and maintained thereat for a predetermined period of time which may range from about 0.5 up to about 10 hours or more in duration. At the end of this time, heating is discontinued and after the autoclave and contents thereof have returned to room temperature, the excess pressure is discharged, the autoclave is opened, and the reaction mixture is recovered therefrom. After separation from the catalyst, the reaction products are subjected to conventional means of separation which may include fractional distillation whereby the desired isomers of o-cresol, m-cresol and p-cresol are separated and recovered.

Alternatively, the isomerization reaction may be effected in a continuous manner of operation. When this type of operation is utilized, a quantity of the catalyst is placed in an appropriate apparatus which is maintained at the proper operating conditions of temperature and pressure. Following this, the o-cresol or m-cresol which is to be isomerized is continuously charged to this reactor along with the hydrogen. After passage through the reactor for a predetermined period of time, the reactor effluent is continuously withdrawn and subjected to conventional means of separation whereby the desired isomers are separated and recovered, the unreacted o-cresol or m-cresol being recycled to the reactor to form a portion of the feedstock thereto.

Inasmuch as the catalyst is in solid form, various types of continuous reactions may be employed. For example, the catalyst may be maintained in the reactor as a fixed bed and the feedstock passed over the catalyst bed in either an upward or downward flow. Another type of continuous operation which may be effected comprises a moving bed type in which the catalyst and the feedstock are passed through the reactor either concurrently or countercurrently to each other. Alternatively, if so desired, the catalyst may be carried into the reactor as a slurry in the feedstock.

The following examples are given for purposes of illustrating the results which are obtained when utilizing the improvements set forth in the present specification and appended claims. However, it is to be understood that these examples are merely illustrative in nature and that the present invention is not necessarily limited thereto.

EXAMPLE I

As an illustration of a batch type operation, 20 grams of o-cresol along with 10 grams of a crystalline aluminosilicate zeolite catalyst was placed in an autoclave. The autoclave was sealed and nitrogen pressed in until an initial operating pressure of 15 atmospheres had been reached. The autoclave was then heated to a temperature of 250° C. and maintained thereat for a period of one hour. At the end of this time, heating was discontinued and after the autoclave had returned to room temperature, the excess pressure was discharged. The reaction product was recovered and subjected to gas chromatographic analysis, the results being set forth in Table I below under the heading "A".

The above experiment was repeated utilizing 15 atmospheres of hydrogen in place of the nitrogen, the remaining operating conditions of temperature, pressure and time being identical. After recovery of the reaction product, it was subjected to gas chromatographic analysis and the results which were obtained are set forth under heading "B".

TABLE I

|  | A | B |
| --- | --- | --- |
| Light Ends | 11.2 | 5.5 |
| o-cresol | 28.9 | 41.2 |
| m-cresol | 35.8 | 35.5 |
| p-cresol | 12.3 | 12.3 |
| Heavies | 11.8 | 5.5 |
| o-cresol conversion | 71.1 | 58.8 |
| Selectivity % |  |  |
| lights | 15.7 | 9.4 |
| m-cresol | 50.4 | 60.4 |
| p-cresol | 17.3 | 20.9 |
| heavies (xylenols) | 16.6 | 9.4 |

The results set forth in the above Table indicate that when the isomerization reaction was effected in the presence of added hydrogen, there was less loss of aromaticity and less formation of xylenols as well as a greater selectivity to m-cresol and p-cresol than was obtained when utilizing nitrogen, an inert gas, to provide the operating pressure.

EXAMPLE II

An isomerization catalyst was prepared by slurring 500 grams of the sodium form of a crystalline aluminosilicate zeolite known as ZSM-5 in 1,000 grams of a 13% nitric acid solution, said slurrying being effected in a 5,000 mm flask equipped with a Teflon blade stirrer. The mixture was stirred for a period of ½ hour at room temperature and filtered. The solid zeolite was then slurried in 1,000 grams of deionized water and stirred for a period of 10 minutes. Following filtration, the washing procedure was repeated an additional four times. When the pH reached normal, the zeolite was dried for a period of 16 hours at a temperature of 110° C. followed by calcination at a temperature of 350° C. for a period of 1 hour and 550° C. for a period of 4 hours.

The isomerization of o-cresol was effected by placing 22 cc (10.3 grams) of the catalyst prepared according to the above paragraph in a reactor having a ½" inner diameter. Following this, o-cresol was charged to the reactor at a Liquid Hourly Space Velocity of 1.0 hrs.$^{-1}$ while maintaining a pressure of 60 atmospheres and a temperature of 380° C. After a period of 20 hours, the Liquid Hourly Space Velocity was increased to 3.0 hrs.$^{-1}$ for an additional period of 20 hours. The reactor effluent was subjected to gas chromatographic analysis and the results obtained were tabulated in Table II below:

locity of 1.0, the conversion dropping only from 55% to 52% during the reaction period. In addition, the selectivity to p-cresol was maintained at a uniform rate of from about 22% to about 23% as compared to the selectivity rate obtained when no hydrogen was added, i.e.,

TABLE II

| Hrs. on stream | LHSV, hrs.$^{-1}$ | GAS CHROMATOGRAPHIC ANALYSIS | | | | | o-cresol % conversion | Selectivity to p-cresol % |
| --- | --- | --- | --- | --- | --- | --- | --- | --- |
| | | Phenol | o-cresol | m-cresol | p-cresol | heavies | | |
| 4 | 1.0 | 3.3 | 42.7 | 37.9 | 12.6 | 3.6 | 57.3 | 22.0 |
| 8 | 1.0 | 3.6 | 44.5 | 37.1 | 12.0 | 2.9 | 55.5 | 21.6 |
| 12 | 1.0 | 23. | 48.2 | 35.6 | 11.5 | 2.3 | 51.8 | 22.2 |
| 16 | 1.0 | 1.8 | 51.6 | 33.8 | 10.7 | 2.0 | 48.4 | 22.1 |
| 20 | 1.0 | 1.5 | 52.6 | 33.6 | 10.3 | 1.9 | 47.4 | 21.7 |
| 24 | 3.0 | 1.0 | 62.5 | 27.1 | 7.9 | 1.5 | 37.5 | 21.4 |
| 28 | 3.0 | 0.5 | 76.6 | 17.3 | 4.6 | 1.0 | 23.4 | 19.7 |
| 32 | 3.0 | 0.4 | 78.6 | 15.8 | 4.1 | 1.1 | 21.4 | 19.2 |
| 36 | 3.0 | 0.4 | 79.9 | 14.9 | 3.9 | 1.0 | 20.1 | 19.4 |
| 40 | 3.0 | 0.4 | 80.8 | 14.2 | 3.6 | 1.0 | 19.2 | 18.8 |

It is noted from the above Table that the conversion of o-cresol in the absence of added hydrogen dropped from 57% to 47%, while over the 40 hour range, the selectivity to p-cresol varied from 22% to 19%. In addition, the product which was obtained from the isomerization was dark and discolored.

EXAMPLE III

To illustrate the advantages which are obtained when effecting the isomerization of a cresol in the presence of added hydrogen, 20 grams of an isomerization catalyst prepared according to the method set forth in Example II above was placed in a reactor similar in design to that employed in the above example. o-Cresol was charged to the reactor initially at a Liquid Hourly Space Velocity of 1.0 hrs.$^{-1}$ while maintaining the reactor at a temperature of 380° C. and a hydrogen pressure of 60 atmospheres. The charge of o-cresol to the reactor at this Liquid Hourly Space Velocity was maintained for a period of 20 hours following which the Liquid Hourly Space Velocity was increased to 3.0 hrs.$^{-1}$ for an additional period of 24 hours. The reactor effluent was subjected to gas chromatographic analysis at 4 hour intervals and the results are set forth in Table III below:

the selectivity rate dropping from 21% to about 18%. In addition to these advantages, there was also obtained a strong improvement in the color of the product, the product which was obtained when utilizing hydrogen being pale yellow in nature as compared to the dark, discolored product when effecting the isomerization reaction in the absence of hydrogen. A further improvement which was also noted was the presence of less coke on the spent catalyst which was recovered from the hydrogen run as compared to the non-hydrogen run.

EXAMPLE IV

In this example, a catalyst prepared according to the method set forth in the above examples was utilized in the isomerization of m-cresol. The isomerization was effected by placing 20 cc (10.3 grams) of the catalyst in a reactor and charging m-cresol to the reactor, initially at a Liquid Hourly Space Velocity of 1.0 hrs.$^{-1}$ while maintaining the reactor at a temperature of 380° C. and a hydrogen pressure of 60 atmospheres. The hydrogen was charged at an initial 0.4 moles per hour which was increased to 1.2 moles per hour when increasing the Liquid Hourly Space Velocity to 3.0 hrs.$^{-1}$. As in the

TABLE III

| Hrs. on Stream | LHSV, hrs.$^{-1}$ | GAS CHROMATOGRAPHIC ANALYSES | | | | | o-Cresol Conversion % | Selectivity to p-Cresol % |
| --- | --- | --- | --- | --- | --- | --- | --- | --- |
| | | Phenol | o-Cresol | m-Cresol | p-Cresol | Heavies | | |
| 4 | 1.0 | 3.8 | 45.1 | 35.9 | 11.4 | 3.7 | 54.9 | 20.8 |
| 8 | 1.0 | 2.4 | 43.0 | 36.7 | 12.7 | 3.1 | 57.0 | 22.3 |
| 12 | 1.0 | 1.7 | 45.3 | 38.4 | 12.7 | 1.9 | 54.7 | 23.2 |
| 16 | 1.0 | 1.4 | 47.4 | 36.8 | 12.2 | 2.2 | 52.6 | 23.2 |
| 20 | 1.0 | 1.2 | 48.5 | 36.3 | 11.8 | 2.1 | 51.5 | 22.9 |
| 24 | 3.0 | 0.7 | 58.0 | 30.2 | 9.6 | 1.5 | 42.0 | 22.9 |
| 28 | 3.0 | 0.3 | 65.9 | 24.9 | 7.8 | 1.1 | 34.1 | 22.9 |
| 32 | 3.0 | 0.3 | 67.4 | 23.7 | 7.5 | 1.1 | 32.6 | 23.0 |
| 36 | 3.0 | 0.3 | 67.8 | 23.4 | 7.4 | 1.1 | 32.2 | 23.0 |
| 40 | 3.0 | 0.3 | 68.3 | 22.9 | 7.3 | 1.1 | 31.7 | 23.0 |
| 44 | 3.0 | 0.3 | 68.4 | 23.0 | 7.0 | 1.2 | 31.6 | 22.2 |

It is apparent from a comparison of the results set forth in Table III to Table II that when effecting the isomerization reaction in the presence of added hydrogen, a steadier conversion of the o-cresol is obtained, especially when employing a Liquid Hourly Space Veabove examples the reactor effluent was subjected to gas chromatographic analyses at 4 hour intervals. The results of this isomerization are set forth in Table IV below:

TABLE IV

| Hrs. on Stream | LHSV, Hrs.$^{-1}$ | GAS CHROMATOGRAPHIC ANALYSIS | | | | | o-Cresol Conversion % | Selectivity to p-Cresol % |
| --- | --- | --- | --- | --- | --- | --- | --- | --- |
| | | Phenol | o-Cresol | m-Cresol | p-Cresol | Heavies | | |
| 4 | 1.0 | 8.2 | 23.4 | 50.3 | 16.3 | 1.3 | 49.7 | 32.8 |
| 8 | 1.0 | 3.7 | 17.9 | 59.5 | 18.1 | 0.7 | 40.5 | 44.7 |
| 12 | 1.0 | 2.5 | 14.2 | 64.8 | 18.3 | 0.5 | 35.5 | 51.1 |

TABLE IV-continued

| Hrs. on Stream | LHSV, Hrs.$^{-1}$ | GAS CHROMATOGRAPHIC ANALYSIS | | | | | o-Cresol Conversion % | Selectivity to p-Cresol % |
| --- | --- | --- | --- | --- | --- | --- | --- | --- |
| | | Phenol | o-Cresol | m-Cresol | p-Cresol | Heavies | | |
| 16 | 1.0 | 1.6 | 11.2 | 68.1 | 18.5 | 0.3 | 31.6 | 58.5 |
| 20 | 1.0 | 1.1 | 8.9 | 72.6 | 17.1 | 0.3 | 28.4 | 60.2 |
| 24 | 3.0 | 0.5 | 5.5 | 80.0 | 13.9 | 0.1 | 20.0 | 69.5 |
| 28 | 3.0 | 0.2 | 2.5 | 88.0 | 9.3 | 0 | 12.0 | 77.5 |
| 32 | 3.0 | 0.3 | 2.1 | 88.8 | 8.9 | 0 | 11.2 | 79.5 |
| 36 | 3.0 | 0.2 | 1.8 | 90.0 | 7.9 | 0 | 10.0 | 79.0 |
| 40 | 3.0 | 0.3 | 1.7 | 90.1 | 7.9 | 0 | 9.9 | 79.8 |

It is to be noted that although the conversion of the m-cresol decreased during the run, the selectivity to p-cresol increased to a point where a fairly constant selectivity of from 79% to 80% was attained, thus rendering the process attractive for obtaining a highly desirable product, namely p-cresol.

We claim as our invention:

1. In a process for the isomerization of a cresol which comprises treating said cresol in the presence of a catalyst comprising a crystalline aluminosilicate zeolite at isomerizing conditions and recovering the resultant isomerized product, the improvement which comprises effecting said isomerization treatment in the presence of hydrogen in a mole ratio in the range of from about 1:1 to about 10:1 moles of hydrogen per mole of cresol.

2. The process as set forth in claim 1 in which said isomerizing conditions include a temperature in the range of from about 250° to about 450° C. and a pressure in the range of from about 2 to about 75 atmospheres.

3. The process as set forth in claim 1 in which said treatment is effected at a Liquid Hourly Space Velocity in the range of from about 0.1 to about 6 hrs.$^{-1}$.

4. the process as set forth in claim 1 in which said crystalline aluminosilicate zeolite is present in an acid-acting form.

5. The process as set forth in claim 4 in which said crystalline aluminosilicate zeolite possesses a constraint index of from about 1.0 to about 12.0.

6. The process as set forth in claim 1 in which said cresol is o-cresol and said isomerized product comprises m-cresol and p-cresol.

7. The process as set forth in claim 1 in which said cresol is m-cresol and said isomerized product comprises p-cresol and minor amounts of o-cresol.

* * * * *